United States Patent [19]

Whitesides et al.

[11] Patent Number: 4,732,853

[45] Date of Patent: Mar. 22, 1988

[54] METHOD OF MAKING CHIRAL EPOXY ALCOHOLS

[75] Inventors: George M. Whitesides, Newton, Mass.; Wolfgang Ladner, Herbstein-5-Lanzenhain, Fed. Rep. of Germany

[73] Assignee: President and Fellows of Harvard College, Cambridge, Mass.

[21] Appl. No.: 673,994

[22] Filed: Nov. 21, 1984

[51] Int. Cl.$^4$ .................. C12P 17/02; C12N 9/08; C12N 9/18; C07P 41/00

[52] U.S. Cl. .................. 435/123; 435/192; 435/197; 435/198; 435/280

[58] Field of Search ............ 435/123, 192, 197, 280, 435/198

[56] References Cited

PUBLICATIONS

Katsuki et al., J.A.C.S., vol. 102, 5974–5976 (1980).
Sharpless et al., Pure & Appl. Chem., vol. 55, 589–604 (1983).
Ito et al., J.A.C.S., vol. 103, 6739–6741 (1981).
Iriuchijima, Agric. Biol. Chem., vol. 46, 1593–1597 (1982).
Lavayre et al., Biotech. and Bioengin., vol. 24, 2175–2187 (1982)d.
Schneider et al., Agnew. Chem. Int. Ed. Engl., vol. 23, 64–68 (1984).
Tang, J. Biol. Chem., vol. 246, 4510–4517 (1971).
McCaul et al., Biochem. and Biophys. Res. Comm., vol. 72, 1028–1034 (1976).
Hanada et al., Agric. Biol. Chem., vol. 42, 523–541 (1978).
Sugita et al., J. Biochem., vol. 87, 339–341 (1980).

*Primary Examiner*—Charles F. Warren
*Assistant Examiner*—Elizabeth A. Hanley

[57] ABSTRACT

Racemic carboxylic acid esters of epoxy alcohols are enantio selectively hydrolyzed with hydrolytic enzymes to provide chiral epoxy alcohol and chiral unhydrolyzed ester.

11 Claims, 1 Drawing Figure

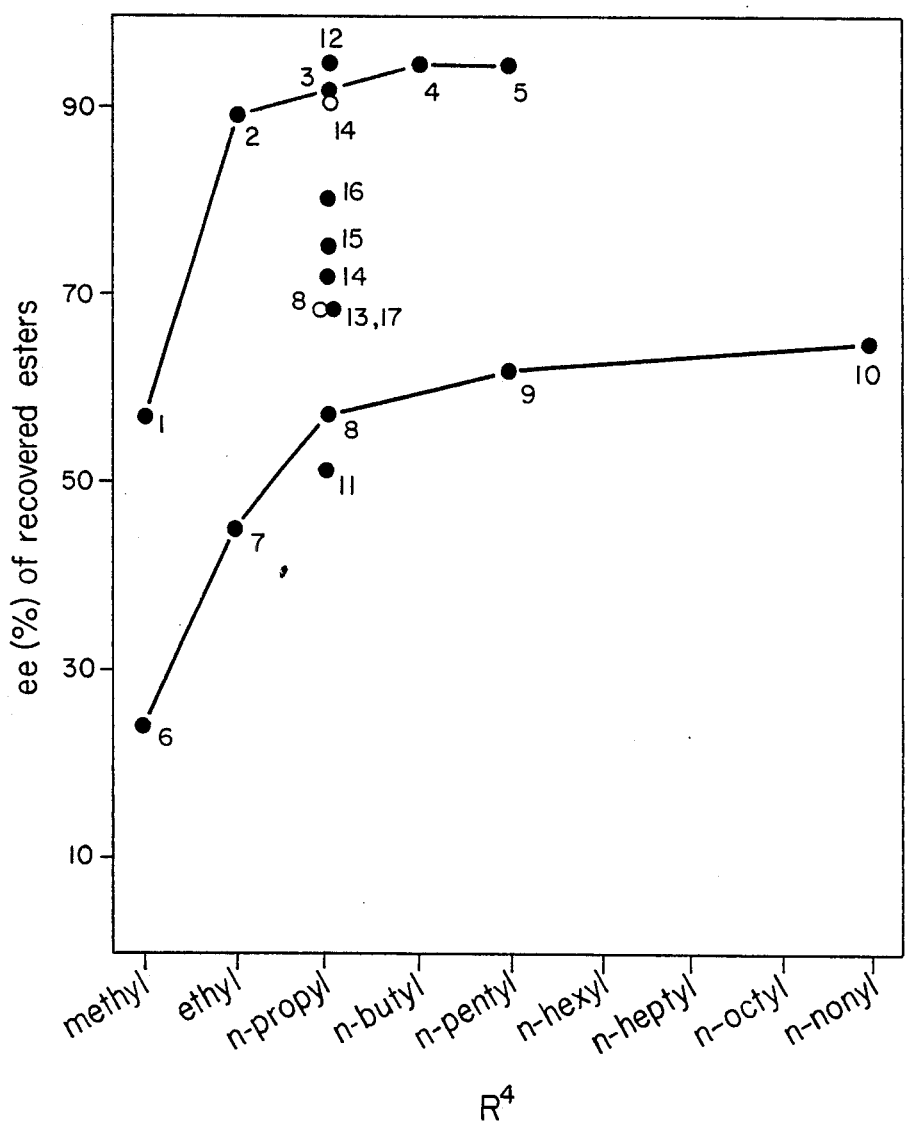

METHOD OF MAKING CHIRAL EPOXY ALCOHOLS

The invention described herein was made with Government support under Grant GM 3067 awarded by the National Institutes of Health, and the U.S. Government has certain rights in the invention.

This invention relates to a method of making chiral epoxy alcohols from racemic carboxylic acid esters of said alcohols and pertains more specifically to partial enzymatic hydrolysis of racemic carboxylic acid esters to form chiral epoxy alcohols and chiral unhydrolyzed esters of opposite chirality which esters can subsequently be separately hydrolyzed to chiral epoxy alcohols of opposite chirality to the first.

It has previously been proposed to employ transition metal catalysis of epoxidation of non-chiral allylic alcohols to form chiral epoxy alcohols as described for example by Katsuki et al., J.A.C.S., Vol. 102, 5974–5976 (1980) and Sharpless et al., Pure & Appl. Chem., Vol. 55, 589–604 (1983). It has also been proposed to employ enzymes and microorganisms for enantioselective hydrolysis of certain esters, as described for example by Ito et al., J.A.C.S., Vol. 103, 6739–6741 (1981); Iriuchijima, Agric. Biol. Chem., Vol. 46, 1593–1597 (1982); Lavayre et al., Biotech. and Bioengin., Vol. 24, 2175–2187 (1982)d; and Schneider et al., Angew. Chem. Int. Ed. Engl., Vol. 23, 64–68 (1984). However, it has been generally known in the art that enzymes are reactive with, hence inactivated by, epoxides particularly by epoxides related to substrates for the enzymes. See for example, Tang., J. Biol. Chem., Vol. 246, 4510–4517 (1976) McCaul et al., Biochem. and Biophys. Res. Comm., Vol. 72, 10928–1034 (1976); Hanada et al., Agric. Biol. Chem., Vol. 42, 523–541 (1978); Sugita et al., J. Biochem., Vol. 87, 339–341 (1980).

It has now been found that despite the known inactivating effect of epoxides on enzymes, racemic carboxylic acid esters of epoxy alcohols are enantioselectively hydrolyzed by enzymatic catalysis to form chiral epoxy alcohols in good yield together with chiral unhydrolyzed ester. The racemic carboxylic acid esters of epoxy alcohols which can be employed in the process of the present invention include those having the following structure:

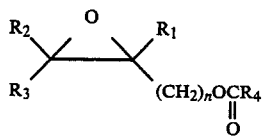

in which $R_1$, $R_2$ and $R_3$ are independently hydrogen or alkyl groups having 1 to 5 carbon atoms, $R_4$ is an alkyl group having from 1 to 20 carbon atoms, preferably from 3 to 10 carbon atoms, either straight or branched chain, or an aryl group having 6 to 8 carbon atoms, and n is 1–5.

In the drawing, the figure is a graphical summary of the enantiomeric properties of numerous different epoxy alcohol esters partially hydrolyzed in accordance with the present invention.

Any of the usual hydrolytic enzymes employed for enantioselective hydrolysis can be used in the present invention; among those which can be used are pig liver esterase, pancreatin, lipases, such as steapsin (lipase from porcine pancreas extract), lipase from *Candida cylindracea*, lipase from *Rhizopus arrhizus*, cholinesterases such as acetyl cholinesterase, butyryl cholinesterase, and alpha chymotrypsin; of these, porcine pancreas lipase is preferred.

The reaction conditions for the hydrolysis are not critical. The reaction can be carried out in an aqueous medium such as water or a mixture of water with water-soluble organic solvents at a pH from about 5 to about 9 at room temperature, although temperatures from about −20° to 70° C. may be used. Low temperatures often lead to high values of enantiomeric excess, although rates may be slower at low temperatures. In general no water-soluble organic solvent is needed, the reaction occurring in a two phase system of water and water insoluble esters. It is desirable to employ a buffer to maintain the pH within the desired range during the course of reaction, or to use an automatic titrator or pH controller to add an alkali such as sodium or potassium hydroxide for this purpose. The relative amounts of ester and water are not critical and may vary over a wide range, a molar excess of water being preferred. The concentration of enzyme in water is also not critical, nor is the proportion of enzyme to ester critical, both may be varied within wide limits in accordance with generally known procedures for hydrolysis of other esters.

Hydrolysis can be carried to any desired degree of conversion. Of course, 100% conversion corresponds to complete hydrolysis of both enantiomers of the racemic ester mixture used as the starting material. The enantiomeric excess, in the case of unhydrolyzed ester, increases with the extent of hydrolytic conversion in accordance with well known principles, so that simply extending reaction time and extent of conversion yields highly enantiomerically enriched ester, but at the expense of decreased yield. Conversely, the enantiomeric excess in the case of the epoxy alcohol released during enzymatic hydrolysis decreases with extent of conversion. Consequently, depending upon which enantiomer is of primary importance the extent of enzymatic hydrolysis may be chosen to maximize the purity of the desired enantiomer. If the free alcohol product desired is the enantiomer retained in the unhydrolyzed ester, it may be obtained simply by isolating the ester by conventional procedures after conversion has been carried out to the desired extent, then hydrolyzing the residual ester by conventional acid or base procedures. Both the unhydrolyzed ester and the alcohol products of enzymatic hydrolysis can be separated from the carboxylic acid and isolated by conventional procedures. In general, the extent of conversion, i.e. the extent of enzymatic hydrolysis, may vary from about 5% to about 95%, but as a rule the precise extent of conversion selected will depend upon which enantiomer is desired, the extent of enrichment desired, and economics of the procedure.

The following specific examples will illustrate more fully the nature of the present invention without acting as a limitation upon its scope.

A mixture of 300 grams of glycidyl butyrate (2.08 mol) and 300 ml of water was placed in a 1-liter 3 necked flask, equipped with a pH electrode, and the 2-phase mixture was stirred vigorously with a magnetic stirrer. Addition of 7.5 grams of crude porcine pancreas lipase initiated the hydrolysis. The pH was maintained at 7.8 by the addition of 7 molar aqueous sodium hydroxide using a pH controller. When 60% of the theoretical amount of base required to neutralize all of the butyric acid in the butyrate had been added (178 ml, 1.25 mol, 6 hour reaction time at 20° C.) the reaction mixture was poured into 1 liter of dichloromethane. The phases were separated and the aqueous phase reextracted with two 200 ml portions of methylene chloride. The organic solvent extracts were combined and washed with 300 ml of 10% aqueous sodium bicarbonate, then twice with 200 ml portions of water, dried with magnesium sulfate containing a small amount of sodium carbonate, and concentrated on a rotary evaporator. Distillation yielded 107 grams of glycidyl butyrate (0.74 mol, 89% based on theoretical yield of one enantiomer). The enantiomeric excess of the product was greater than 92%, as determined by means of a conventional chiral shift reagent, tris[3-(heptafluoropropylhydroxymethylene)-d-camphorato] europium (III).

Recovery of the free alcohol from the reaction mixture was easily accomplished by conventional extraction procedures; the value of the enantiomeric excess of the alcohol was low (below 65%) because the extent of conversion was selected to give high enantiomeric excess for the ester product.

Similar procedures were employed using a variety of other epoxy alcohol esters of carboxylic acids having the following structure:

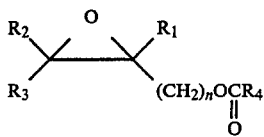

in which $R_1$, $R_2$ $R_3$ were as shown in the following table; n was 1 in the case of compounds 1–14, and n was 2 in the case of compounds 15–17:

| Cmpd | $R^1$ | $R^2$ | $R^3$ |
|---|---|---|---|
| 1, 2, 3, 4, 5, 6, 7, 8, 9, 10 | | $C_3H_7$ | |
| 11 | $CH_3$ | | |
| 12 | | $CH_3$ | |
| 13 | | | $CH_3$ |
| 14 | $CH_3$ | | $CH_3$ |
| 15 (n = 2) | | | |
| 16 (n = 2) | | $C_2H_5$ | |
| 17 (n = 2) | | | $C_2H_5$ |

In the case of all compounds, $R_4$ varied for methyl to n-nonyl as shown along the abscissa of of the drawing. The enantiomeric excess of the recovered ester in case is shown on the ordinate of the plot, in which solid circles show products obtained at 60% enzymatic hydrolytic conversion and open circles show products of 80% conversion. The values of enzymatic excess plotted at 90% or more are minima because of limitations of the analytical method. Recovery of alcohols from most of the reaction mixtures shown in FIG. 1 was accomplished by conventional extraction in 30–80% yield, with relatively low (30–65%) enantiomeric excess values.

The enantiomeric alcohol present in each of the recovered esters of the reactions shown in FIG. 1 could be isolated by conventional acid or base hydrolysis of the enantiomerically enriched ester.

Kinetic Resolution of the Butyrate Ester of trans-2,3-Epoxylhexan-1-ol

A reaction mixture was made up containing aqueous NaCl solution (10.5 mL of 50 mM solution, 20 or 30% v:v dimethyl formamide (DMF), 3.7 g of the racemic ester substrate, and 2 mL of a solution of crude porcine pancreatic lipase (20 mg/mL). The total volume was 24 mL. The mixture was incubated at either 0° or −10° C. The pH was adjusted with an indicator and maintained at either pH 8 or 6 by addition of 2.5M NaOH. The conversion was monitored by pH-stat and gas chromatography (GC). Unhydrolyzed ester and product were extracted from the reaction mixture with 200 mL of diethyl ether and alcohol, and were recovered by immediately drying with $MgSO_4$. The suspension was filtered and the filtrate was concentrated by evaporation. The residue was dissolved in 50 mL of pentane. Two layers were formed. The lower layer, which contained DMF, was separated and extracted twice with pentane. The combined pentane phases were extracted twice with 20 mL portions of water to remove the alcohol. This aqueous phase was extracted with 40 mL of diethyl ether. The diethyl ether was evaporated and the residue was purified by Kugelrohr distillation. The purity of the alcohol was checked by GC and was >93%. The pentane phase was evaporated and the residue was also purified by Kugelrohr distillation. The purity of the recovered ester was checked by GC and was >95%. Enantiomeric excesses were determined by $^1H$ NMR spectroscopy in the presence of the chiral europium shift reagent $Eu(hfc)_3$. One of the epoxy —CH-groups of the partially resolved ester showed peaks for the two enantiomers at ∼3.6 and 3.7. For the resolved alcohol the —$CH_2$— at C(1) showed peaks at ∼3.8 and 4.0 for the two enantiomers. Results of these experiments are summarized in Table I, using the E value (eq 2 for the enantiomeric excess (ee) of the substrate S, or eq 3 for the ee of the product P) to give the degree of enantiomeric enrichment (Chen, C. S.; Fujimoto, Y.; Girdaukas, G.; Sih, C. S. *J. Am. Chem. Soc.* 1982, 104, 7294–9).

$$E = \frac{\ln((1 - c)(1 - ee(S)))}{\ln((1 - c)(1 + ee(S)))} \qquad \text{eq. 2}$$

$$E = \frac{\ln((1 - c(1 + ee(P)))}{\ln((1 - c(1 - ee(P)))} \qquad \text{eq. 3}$$

TABLE I

Influence of reaction variables on the enantiomeric enrichment of recovered ester.

| temp (°C.) | pH | solv | % conv | ee | E |
|---|---|---|---|---|---|
| −10 | 6 | 20 | 60 | 0.93 | 13.8 |
| 0 | 6 | 20 | 60 | 0.74 | 6.3 |
| −10 | 8 | 20 | 60 | 0.90 | 11.9 |
| 0 | 8 | 20 | 60 | 0.84 | 7.6 |
| −10 | 6 | 30 | 60 | 0.93 | 13.7 |
| 0 | 6 | 30 | 60 | 0.87 | 10.4 |
| −10 | 8 | 30 | 60 | 0.86 | 10.0 |
| 0 | 8 | 30 | 60 | 0.80 | 7.6 |

In this table, "solv" refers to the % of DMF (v:v) in the aqueous solution, and % conv to the total racemic ester hydrolyzed to butyric acid and epoxy alcohol.

The E value for the recovered alcohol and ester are, in principle, identical (so long as no competing non-enzymic reactions cause racemization). Although E values were not routinely determined for both ester and alcohol, in those instances in which comparisons were made the E values were, in fact, indistinguishable within experimental error (±0.05). For example; in a reaction carried to 52% conversion, the alcohol had E=10.1 (corresponding to an enantiomeric excess of 0.66) and the ester has E=10.1 (corresponding to an enantiomeric excess of 0.71).

What is claimed is:

1. The method of making chiral epoxy alcohols and esters which comprises providing a racemic carboxylic acid ester of an epoxy alcohol, bringing said ester into contact with water and a hydrolytic enzyme to hydrolyze said ester to the extent of about 5% to about 95%, and separating the resultant free alcohol from unhydrolyzed ester.

2. The method as claimed in claim 1 in which said enzyme is lipase.

3. The method as claimed in claim 1 in which said racemic ester has the structure

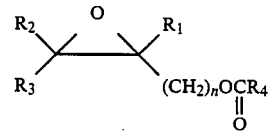

in which $R_1$, $R_2$ and $R_3$ are independently hydrogen or alkyl groups having 1 to 5 carbon atoms, $R_4$ is an alkyl group having from 1 to 20 carbon atoms, or an aryl group having 6 to 8 carbon atoms, and n is 1-5.

4. The method as claimed in claim 3 in which said enzyme is lipase.

5. The method as claimed in claim 4 in which said enzyme is porcine pancreatic lipase.

6. The method as claimed in claim 3 in which said racemic ester is a glycidyl ester.

7. The method as claimed in claim 4 in which said racemic ester is a glycidyl ester.

8. The method as claimed in claim 5 in which said racemic ester is a glycidyl ester.

9. The method as claimed in claim 1 including the additional steps of separately hydrolyzing said unhydrolyzed ester to provide a second free alcohol of opposite chirality to the first resultant free alcohol.

10. The method as claimed in claim 5 including the additional steps of separately hydrolyzing said unhydrolyzed ester to provide a second free alcohol of opposite chirality to the first resultant free alcohol.

11. The method as claimed in claim 6 including the additional steps of separately hydrolyzing said unhydrolyzed ester to provide a second free alcohol of opposite chirality to the first resultant free alcohol.

* * * * *